United States Patent [19]
Sarvazyan

[11] Patent Number: 5,785,663
[45] Date of Patent: Jul. 28, 1998

[54] METHOD AND DEVICE FOR MECHANICAL IMAGING OF PROSTATE

[75] Inventor: Armen Paruir Sarvazyan, East Brunswick, N.J.

[73] Assignee: Artann Corporation, Lambertville, N.J.

[21] Appl. No.: 607,645

[22] Filed: Feb. 27, 1996

Related U.S. Application Data

[63] Continuation-in-part of Ser. No. 994,109, Dec. 21, 1992, Pat. No. 5,524,636.

[51] Int. Cl.$^6$ ........................................................ A61B 8/00
[52] U.S. Cl. ........................................... 600/587; 600/561
[58] Field of Search .................................. 600/567, 561, 600/437–444

[56] References Cited

U.S. PATENT DOCUMENTS

| | | | |
|---|---|---|---|
| 4,250,894 | 2/1981 | Frei et al. | 128/774 |
| 4,423,738 | 1/1984 | Newgard | 128/672 |
| 4,580,574 | 4/1986 | Gavish | 128/774 |
| 4,799,491 | 1/1989 | Eckerle | 128/672 |
| 4,802,488 | 2/1989 | Eckerle | 128/672 |
| 4,860,761 | 8/1989 | Yamasawa et al. | 128/686 |
| 4,947,851 | 8/1990 | Sarvazyan | 128/660.02 |
| 5,078,142 | 1/1992 | Siczek et al. | 128/653.1 |
| 5,099,848 | 3/1992 | Parker et al. | 128/661.07 |
| 5,107,837 | 4/1992 | Ophir et al. | 128/660.01 |
| 5,115,808 | 5/1992 | Popovic et al. | 128/774 |
| 5,178,148 | 1/1993 | Lacoste et al. | 128/660.03 |
| 5,247,937 | 9/1993 | Ophir et al. | 128/661.03 |
| 5,265,612 | 11/1993 | Sarvazyan et al. | 128/660.01 |
| 5,278,776 | 1/1994 | Fisher et al. | 128/774 |
| 5,293,870 | 3/1994 | Ophir et al. | 128/660.01 |
| 5,474,070 | 12/1995 | Ophir et al. | 128/661.003 |

OTHER PUBLICATIONS

C.R. Gentle, *Mammobarography: a possible method of mass breast screening* (1988) J. Biomed. Eng., vol. 10, pp. 124–126.

R.M. Lerner et al., *Sono–Elasticity: Medical Elasticity Images Derived From Ultrasound Signals in Mechanically Vibrated Targets* (1988) Acoustical Imaging, vol. 16, p. 317.

T.A. Krouskop et al., *A Pulsed Doppler Ultrasonic System for Making Non–Invasive Measurement of Mechanical Properties of Soft Tissue* (1987) 24 J. Rehab. Res. Dev., vol. 24, p. 1.

A.P. Sarvazyan et al., *Biophysical Bases of Elasticity Imaging* (1995) Acoustical Imaging, vol. 21, pp. 223–240.

A.P. Sarvazyan et al., *A New Philosophy of Medical Imaging* (1991) Medical Hypotheses, vol. 36, pp. 327–335.

Y. Yamakoshi et al., *Ultrasonic Imaging of Internal Vibration of Soft Tissue Under Forced Vibration* (1990), IEEE Transactions on Ultrasonics, Ferroelectric, and Frequency Control, vol. 7(2), p. 45.

*Primary Examiner*—Robert L. Nasser
*Attorney, Agent, or Firm*—Mathews, Collins, Shepherd & Gould

[57] ABSTRACT

A device and method for visualizing geometrical and mechanical parameters of prostates and diagnosing prostate diseases using a pressure sensor array is disclosed. A probe having an articulated tip for insertion in the rectum applies digital pressure to the prostate similar to that applied by a human finger. A pressure and position/orientation sensor is provided in the tip. Signals from the sensors are used to calculate a virtual pattern of a property such as stress and strain. The virtual and theoretical patterns are compared and differences are used to indicate the presence and location of differing elasticity regions of the tissues being examined and to display an image of the examined prostate.

11 Claims, 10 Drawing Sheets

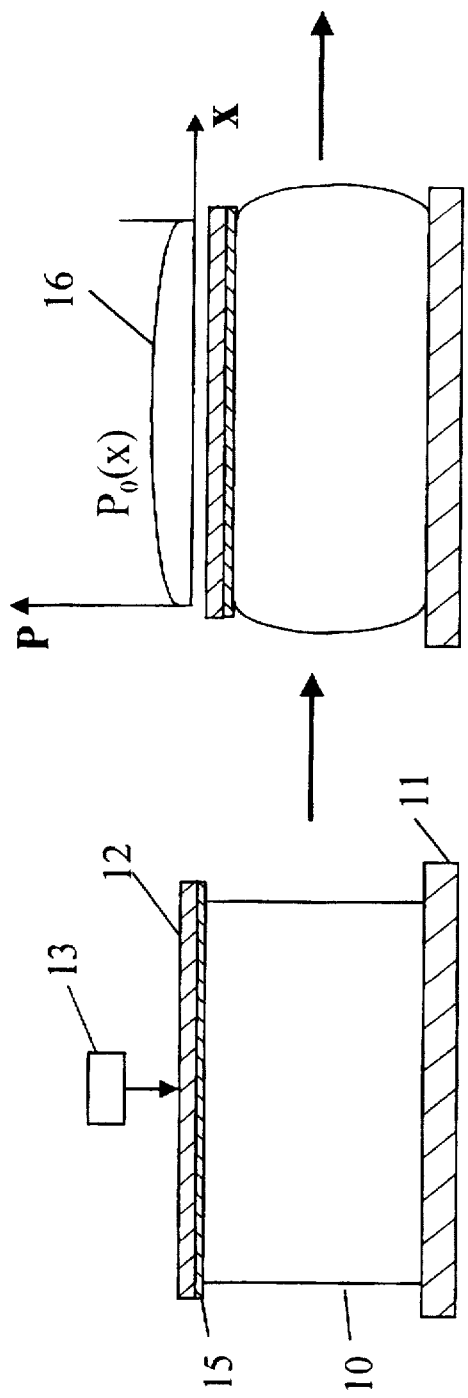
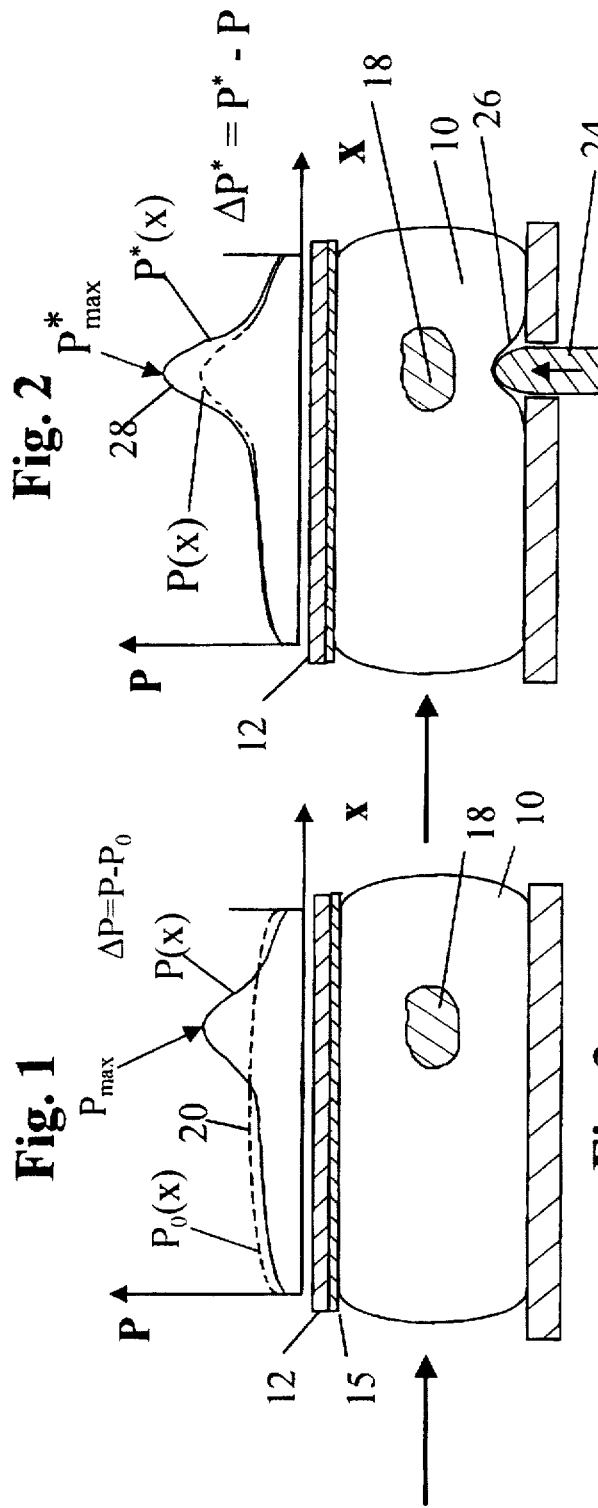
Fig. 1
Fig. 2
Fig. 3
Fig. 4

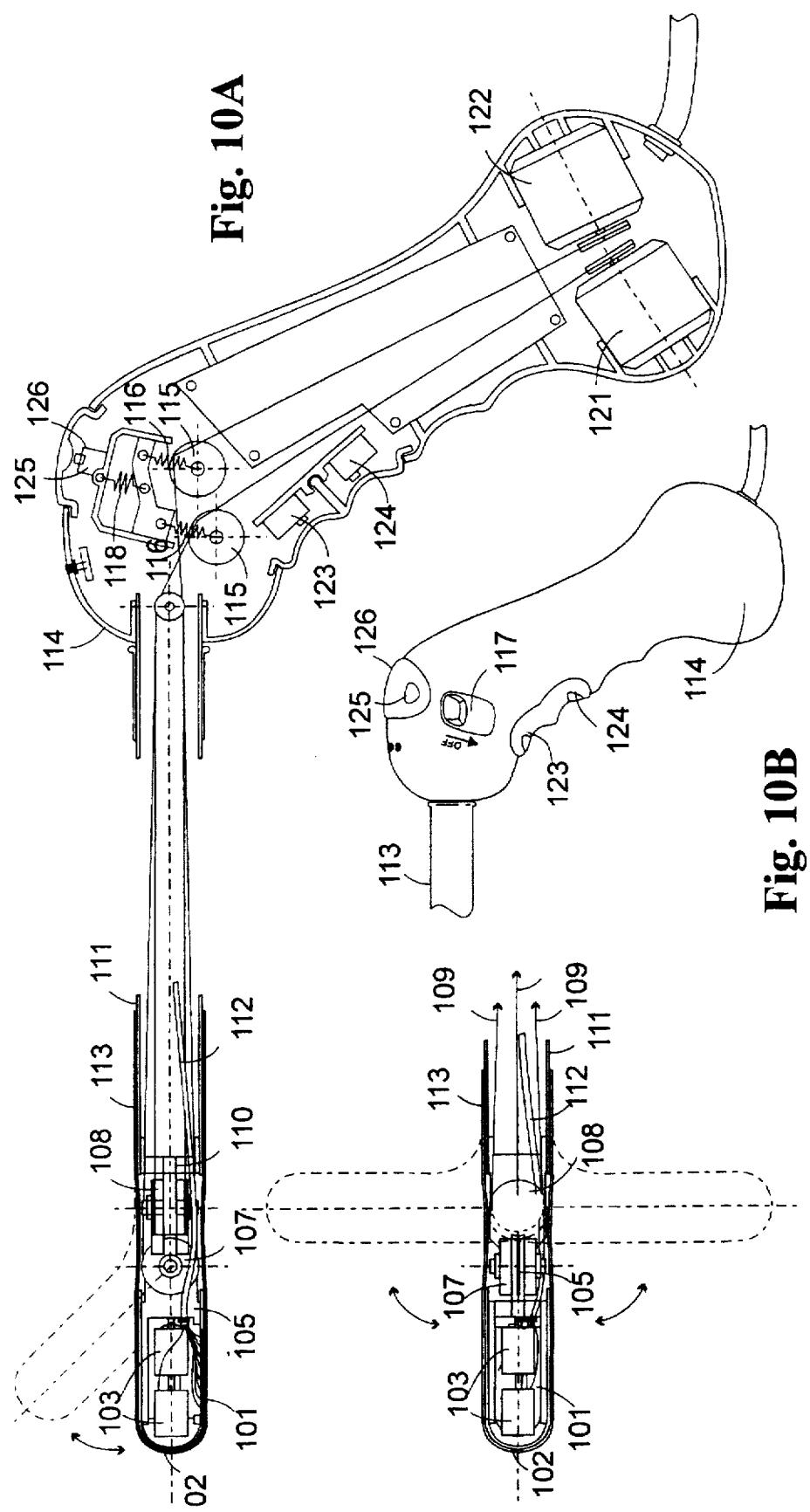

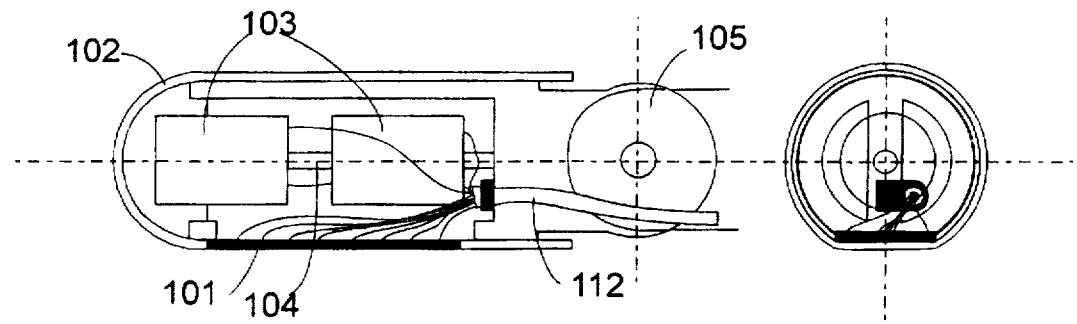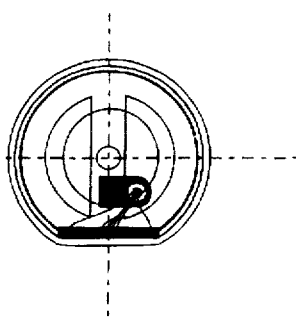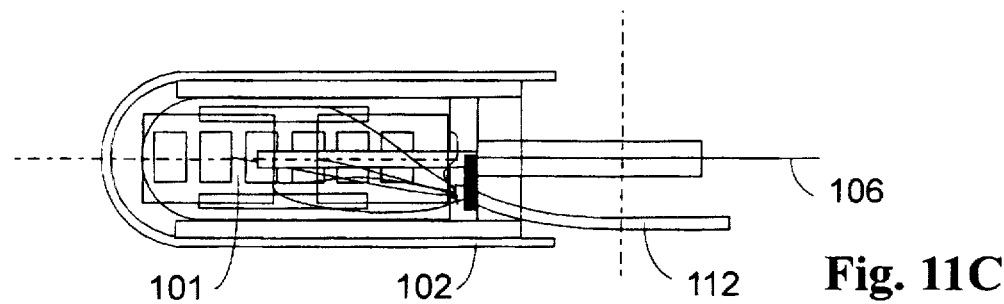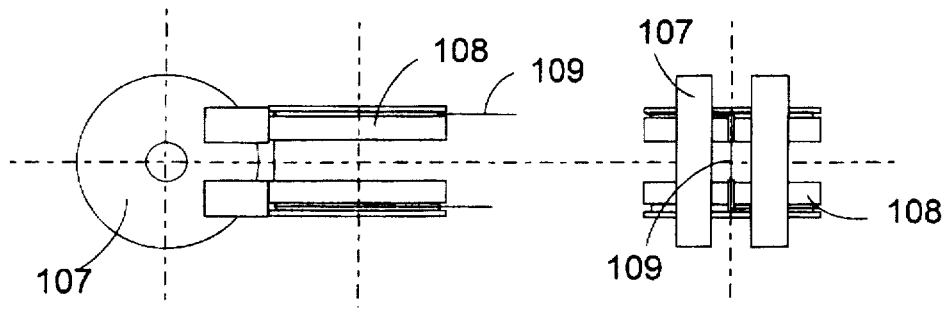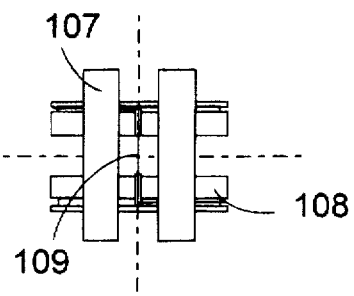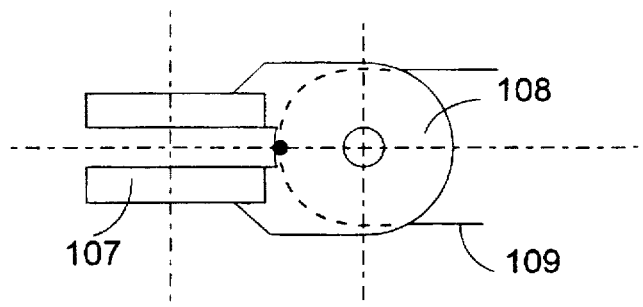

METHOD AND DEVICE FOR MECHANICAL IMAGING OF PROSTATE

CROSS REFERENCE TO RELATED APPLICATION

This application is a continuation-in-part of U.S. patent application Ser. No. 07/994,109, filed Dec. 21, 1992, now U.S. Pat. No. 5,524,636, the full disclosure of which is hereby incorporated herein by reference.

BACKGROUND OF THE INVENTION

1. Technical Field

The present invention relates to a method and apparatus for visualizing geometrical and mechanical parameters of prostate and diagnosing prostate diseases using a pressure sensor array and a position/orientation sensor mounted in the tip of an articulated transrectal probe.

2. Description of the Prior Art

Diagnosing early formation of tumors, particularly those caused by cancer, has been a problem that has been attempted to be solved using various techniques, such as ultrasonic imaging, nuclear magnetic resonance imaging, x-rays, and the like.

One of the safest and oldest techniques of detecting diseased tissue is palpation (digital examination). Palpation, that is, examination using the sense of touch, is based on the significant differences in elasticity of normal tissues and certain lesions. Palpation has been a commonly used technique for detecting prostate and breast cancer. Several authors have proposed various types of devices mimicking palpation to detect tumors using different types of pressure sensors. For example, Frei et al., U.S. Pat. No 4,250,894, have proposed an instrument for breast examination that uses a plurality of spaced piezoelectric strips which are pressed into the body being examined by a pressure member which applies a given periodic or steady stress to the tissue beneath the strips.

A different principle for evaluating the pattern of pressure distribution over a compressed breast was proposed by Gentle (Gentle CR, *Mammobarography: a possible method of mass breast screening*, J. Biomed. Eng. 10, 124–126, 1988). The pressure distribution is monitored optically by using the principle of frustrated total internal reflection to generate a brightness distribution. Using this technique, referred to as "mammobarography," simulated lumps in breast prostheses have been detected down to a diameter of 6 mm. According to Gentle, this technique can be used for mass breast screening; however, no quantitative data on lumps in a real breast was ever published. The failure has been explained by the insufficient sensitivity of the registration system. It should be noted, that most of the development of pressure sensors for medical applications has been done not for mimicking palpation but for monitoring blood pressure and analyzing propagation of pulse waves in blood vessels (See, for example, U.S. Pat. Nos. 4,423,738; 4,799,491; 4,802,488; 4,860,761).

Another approach to evaluate elasticity of the tissues uses indirect means, such as conventional imaging modalities (ultrasound or MRI) which are capable of detecting motion of a tissue subjected to an external force. One approach attempts to determine the relative stiffness or elasticity of tissue by applying ultrasound imaging techniques while vibrating the tissue at low frequencies. See, e.g., K. J. Parker et al, U.S. Pat. No. 5,099,848; R. M. Lerner et al., *Sono-Elasticity: Medical Elasticity Images Derived From Ultrasound Signals in Mechanically Vibrated Targets*, Acoustical Imaging, Vol. 16, 317 (1988); T. A. Krouskop et al., *A Pulsed Doppler Ultrasonic System for Making Non-Invasive Measurement of Mechanical Properties of Soft Tissue*, 24 J. Rehab. Res. Dev. Vol. 24, 1 (1987); Y. Yamakoshi et al., *Ultrasonic Imagine of Internal Vibration of Soft Tissue Under Forced Vibration*, IEEE Transactions on Ultrasonics, Ferroelectrics, and Frequency Control, Vol. 7, No. 2, Page 45 (1990).

Another method proposed for measuring and imaging tissue elasticity is described in Ophir et al., U.S. Pat. Nos. 5,107,837, 5,293,870, 5,143,070 and 5,178,147. This method includes emitting ultrasonic waves along a path into the tissue and detecting an echo sequence resulting from the ultrasonic wave pulse. The tissue is then compressed (or alternatively decompressed from a compressed state) along the path and during such compression, a second pulse of ultrasonic waves is sent along the path into the tissue. The second echo sequence resulting from the second ultrasonic wave pulse is detected and then the differential displacement of selected echo segments of the first and second echo sequences are measured. A selected echo segment of the echo sequence, i.e., reflected RF signal, corresponds to a particular echo source within the tissue along the beam axis of the transducer. Time shifts in the echo segment are examined to measure compressibilities of the tissue regions.

Sarvazyan et al., have recently developed a device for elasticity imaging of the prostate using an ultrasonic transrectal probe (U.S. Pat. No. 5,265,612). This device enables physicians to quantitatively and objectively characterize elasticity moduli of prostate tissues. The elasticity characterization and imaging is achieved by evaluating the pattern of the internal strain in the prostate and surrounding tissues using conventional transrectal ultrasonography. The pattern of internal strain is obtained by ultrasonically imaging the prostate at two levels of its deformation. The deformation is provided by changing the pressure in the fluid filling the sheath surrounding the transrectal probe. In addition to elasticity, other tumor parameters reflecting the stage of its development include the geometrical parameters of the tumor, such as its volume or diameter. Lacoste et al., U.S. Pat. No. 5,178,148, have disclosed a method of determining the volume of a tumor or gland, particularly the prostate, using an endocavity detector probe, in particular, a transrectal probe.

SUMMARY OF THE INVENTION

The method and device for transrectal imaging of prostate of the present invention are based on a new technology of medical imaging described in the generic patent, referred to herein as Mechanical Imaging ("MI"). The essence of MI is the reconstruction of the internal structure of soft body tissues by measuring a surface stress pattern using a pressure sensing array. The pattern of mechanical stress and its changes as a function of applied pressure and time contain comprehensive information on the mechanical properties and geometry of the internal structures of the body tissues.

The most promising applications of MI devices are in those fields of medicine where palpation is proven to be a sensitive tool in detecting and monitoring diseases, including prostate cancer. Palpation, i.e. digital rectal examination (DRE), is currently the most common method of prostate cancer detection. Despite the obvious usefulness of the diagnostic information obtained by DRE, there are no technical means and devices capable of yielding data similar to that obtained by the finger of a skilled examiner. To examine the gland, a physician inserts a finger into the rectum and, feeling the gland through the rectal wall, searches for abnormalities in its size, contour, consistency and localization. A hard, nodular, or indurated prostate discovered on routine DRE may be the first indication of cancer.

A device and a method in accordance with the present invention are based on the use of a transrectal probe having an articulated tip for insertion in the rectum and controls for moving the tip over several degrees of freedom. The tip applies pressure similar to that applied by a human finger. Pressure sensors mounted on the tip measure the localized pressure distribution. A position/orientation sensor is also provided in the tip to determine the position of the tip corresponding to the particular pressure pattern measured by the pressure sensor array. Signals from the pressure sensor array and position/orientation sensor are used to calculate a virtual pattern of a property such as stress and strain for the examined prostate. A theoretical geometrical model of the examined prostate is defined assuming that the tissue is homogeneous and has dimensions estimated from the measurement data. Theoretical patterns of stress and strain are then evaluated using said theoretical geometrical model. The virtual pattern and theoretical pattern of strain or stress are compared and differences indicate location and relative hardness of a differing elasticity region. The theoretical geometrical model is then adjusted by varying the spatial distribution of elasticity to minimize the differences. This adjustment of the geometrical and mechanical parameters of model is iteratively repeated until said differences become less than a preselected level. Thus, an inverse mechanical problem is solved and a spatial distribution of elasticity modulus is obtained in the tissue portion being examined. The resultant distribution is used to construct and display an image of the examined prostate.

Before referring specifically to the drawings, and without being bound by any particular posited theory, the theoretical aspects of the invention are discussed. Pressure pattern on the surface of an investigated tissue portion together with given boundary conditions enable one to reconstruct internal structures in underlying tissue and to evaluate relative hardness and softness of tissue in localized areas. The present invention utilizes the relationship between elasticity differences in localized areas inside of tissue, the stress pattern on the surface of the tissue, and internal strain pattern. This relationship forms the theoretical basis for a method of detecting and quantifying tissue abnormalities.

When calculating the mechanical properties of tissues, calculations are based on a model of the tissue as being linearly elastic and incompressible media. Such an approach is a first approximation which is sufficient to solve all questions arising in mechanical elasticity imaging.

Accordingly, the graphical representations discussed in the detailed description of the invention are based on calculations from the general equations presented below. The following equations are general equations for three dimensional linear theory of elasticity for in-compressible media like tissues or another water based system, that is a system having a Poisson's ratio of 0.5 (Sarvazyan et al., *Biophysical Bases of Elasticity Imaging*, Acoustical Imaging, Vol. 21, 223, 1995).

The equations for dynamic equilibrium are:

$$\frac{\partial \sigma_{xx}}{\partial x} + \frac{\partial \sigma_{xy}}{\partial y} + \frac{\partial \sigma_{xz}}{\partial z} = \rho \frac{\partial^2 U}{\partial t^2} \quad (1)$$

-continued $$\frac{\partial \sigma_{xy}}{\partial x} + \frac{\partial \sigma_{yy}}{\partial y} + \frac{\partial \sigma_{yz}}{\partial z} = \rho \frac{\partial^2 V}{\partial t^2}$$

$$\frac{\partial \sigma_{xz}}{\partial x} + \frac{\partial \sigma_{yz}}{\partial y} + \frac{\partial \sigma_{zz}}{\partial z} = \rho \frac{\partial^2 W}{\partial t^2}$$

Where:
U, V, W are components of displacement;
$\rho$ is density of media; and
$\sigma_{ij}$ are components of stress tensor.

The pattern of stresses must be related to a pattern of strain. This relationship for incompressible media (e.g. tissues or other water based systems) is given by the following equations:

$$\sigma_{xx} = P + 2\mu E_{xx} \quad \sigma_{yy} = P + 2\mu E_{yy} \quad \sigma_{zz} = P + 2\mu E_{zz} \quad (2)$$
$$\sigma_{xy} = 2\mu E_{xy} \quad \sigma_{xz} = 2\mu E_{xz}, \quad \sigma_{yz} = 2\mu E_{yz}$$

where $\mu = \frac{E}{2(1+\nu)}$, $\nu = 0.5$ is Poisson's ratio, $E$ is Young's Modulus, and $$E_{xx} = \frac{\partial U}{\partial x} \quad E_{yy} = \frac{\partial V}{\partial y} \quad E_{zz} = \frac{\partial W}{\partial z}$$

$$E_{xy} = \frac{1}{2}\left(\frac{\partial U}{\partial y} + \frac{\partial V}{\partial x}\right) \quad E_{xz} =$$

$$\frac{1}{2}\left(\frac{\partial U}{\partial x} + \frac{\partial W}{\partial z}\right) E_{yz} = \frac{1}{2}\left(\frac{\partial V}{\partial z} + \frac{\partial W}{\partial y}\right)$$

By combining equations (1) and (2), we can obtain three equations containing only three unknowns, U, V, W, which are components of displacement plus the unknown pressure P.

An additional equation is the equation of incompressibility showing that divergence of vector displacement equals zero:

$$\frac{\partial U}{\partial x} + \frac{\partial V}{\partial y} + \frac{\partial W}{\partial z} = E_{xx} + E_{yy} + E_{zz} = 0$$

This last equation represents the condition that when force is applied to the soft tissue, all the deformation of tissue is related to changes of the shape of the soft tissue but not the volume, because Poison's ratio is 0.5, that is the bulk compressional modulus of soft biological tissues is many orders of magnitude higher then the shear elasticity modulus.

The characteristics of living tissue not only involve elasticity as discussed, but also viscosity. Thus, the tissue is a viscoelastic material that requires description in both viscous and elastic components. Viscosity affects the information received because with a viscoelastic tissue, there is a time delay between force application and any displacement that occurs. In a dynamic mode where force is applied in time, the development of stresses in time provides the information on viscosity.

In case of viscoelastic media, the components of the stress tensor in equation (2) should have following additional terms for shear viscosity, $\mu^*$ $$2\mu^* \frac{\partial E_{ij}}{\partial t}$$

The shear modulus and Young's modulus of soft tissue are different by a factor of 3, because Poisson's ratio is 0.5.

While either modulus can be used for examination of the tissue, Young's modulus is used in the description of the present invention.

In the case of harmonic disturbances, temporal dependence can be easily removed from these equations and the system of the differential equations for amplitudes will be obtained.

With the foregoing and other objects, advantages and features of the invention that will become hereinafter apparent, the nature of the invention may be more clearly understood by reference to the following detailed description of the invention, the appended claims and the several views illustrated in the drawing.

BRIEF DESCRIPTION OF THE DRAWINGS

FIG. 1 is a schematic representation of a model of soft "tissue" illustrating a device for loading incorporating pressure sensors used in the present invention;

FIG. 2 the device of FIG. 1 after loading the tissue, and illustrating a typical pressure curve across a surface of the tissue;

FIG. 3 is similar to the tissue compression in FIG. 2, illustrating the effect of a presence of a tumor in the tissue;

FIG. 4 is an illustration of the structure shown in FIG. 3, with a piston deforming tissue from a side opposite from the pressure plate;

FIG. 10A is a side sectional view of a transrectal probe in accordance with the present invention;

FIG. 10B is a retail view of a pistol grip handle for a transrectal probe in accordance with the present invention;

FIG. 10C is the top view of an articulated probe tip;

FIGS. 11A-C detail views of the probe tip showing a pressure sensor array and a position/orientation sensor;

FIGS. 12A-C detail views of the probe joint which permits articulation of the probe tip;

DETAILED DESCRIPTION OF THE INVENTION

Figure 5:
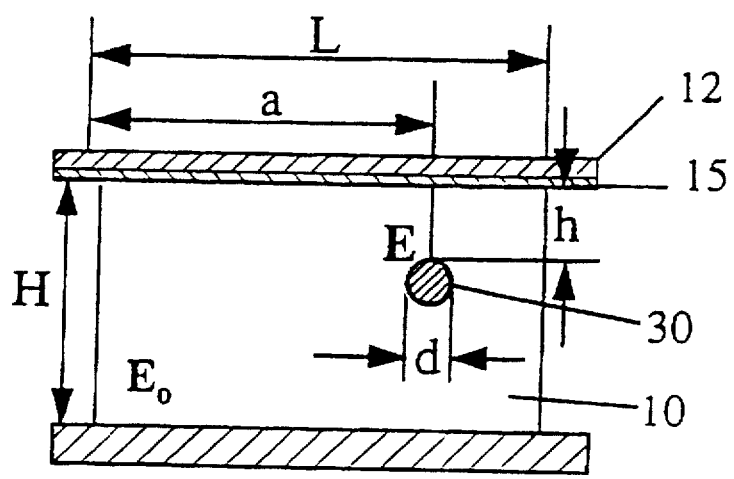
FIG. 5 is schematic illustration of loading parameters for a model tissue being examined and a tumor in such tissue; differential pressure ratio.

Referring now to the drawings, like elements are designated by like numerals. FIG. 1 illustrates a portion of a soft tissue 10 that is supported on a base 11 which supports a flat rigid plate 12 capable of exerting pressure thereon from a force generator 13. A series of individual pressure sensors indicated at 15 are provided on the bottom surface of the plate 12 to sense pressure in an array across the surface of tissue 10.

FIG. 2 represents a pressure profile P(x) of the homogeneous tissue 10 when deformed. FIG. 3 illustrates a homogeneous tissue pressure profile in the dotted line and the profile of tissue 10 having an inclusion 18 in the solid line. The difference between these two pressure profiles shown in FIG. 3 provides information on the presence, location, and relative elasticity of inclusion 18 with respect to surrounding tissue 10. The strain pattern on the surface of the tissue 10 as shown in FIG. 3 is in this case represented in the form of pressure profile P(x). This strain pattern depends on the presence of an inclusion 18, as well as on the dimension of the tissue 10, neighboring anatomical features of that tissue, such as presence of a bone, and on the geometrical relationship of the tissue 10, support member 11 and deformation member 12. Therefore, the difference between the measured profile P(x) and the profile $P_o(x)$, shown by the dotted line, theoretically calculated for a homogenous model of that tissue under same boundary conditions, contains direct information on the inclusion, rather than the strain profile P(x) itself.

FIG. 4 schematically illustrates how the present invention enhances the amplitude of the pressure profile and, thus, improves detection of an inclusion. In this instance, the tissue 10 is supported on a base 11, and a schematically shown piston or block 24 which also is called a "finger" as used in palpation, is provided on the base and is caused to protrude into the tissue and compress the tissue in a localized area indicated at 26 directly below inclusion 18, which can be a tumor.

The represented pressure profile schematically disposed on the top of the pressure plate 12 (which is displaced the same as that previously explained) represents the data provided by the pressure sensors 15. P(x) is represented as a dashed line and is the profile substantially as that shown in FIG. 3. P*(x), indicated by line 28, represents the pressure profile resulting from the presence of the piston 24 directly under the tumor. The piston 24 acts like a probe to cause extra compression in the desired region (e.g., inclusion 18) in addition to the general compression of the tissue 10 between plate 12 and base 11. This results in a substantial increase in the pressure profile P*(x) which reaches a maximum at $P^*_{max}$ directly over the tumor. By comparing the respective pressure profiles P(x) and P*(x), one can recognize that a much greater amplitude of the pressure profile can be obtained from the pressure sensors (to indicate an abnormality) when a probe (e.g., piston 24) or other extra compressive force is directed in the region of a tumor. In this case, a change in the pressure profile amplitude because of the piston 24 is represented as $\Delta P^* = P^* - P$.

FIGS. 5-9 are schematic examples to illustrate the applicability of the theory to the methods and devices disclosed, and to show the range of variables and measured parameters available for calculating meaningful values for quantitative analysis and evaluation. The illustrations of tissue are not meant to represent any particular portion of a human body.

Figure 5A:
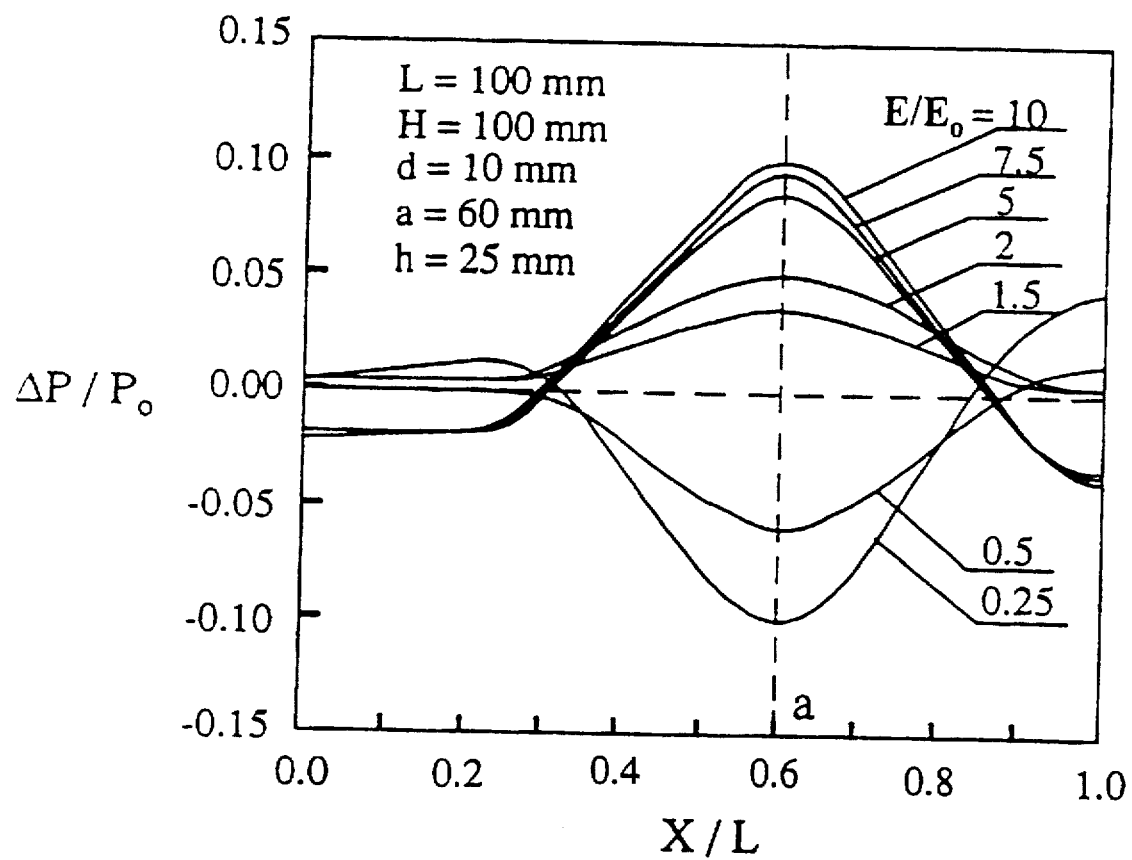
FIG. 5A is a plot of calculated differential pressure ratio across the surface at differing ratios of moduli of elasticity ratio between surrounding tissue and a tumor.

In FIG. 5, a schematic representation illustrates tissue having a tumor therein of a certain size and location. The graph of FIG. 5A illustrates a particular calculated differential pressure ratio as a function of the distance along the horizontal axis on the surface of the tissue. The graph is based on the dimensions shown in FIG. 5 having certain values, such as those listed in FIG. 5A. The symbol (E) represents the elasticity modulus (Young's modulus) of the tumor and ($E_O$) represents the elasticity modulus (Young's modulus) of the surrounding tissue. A ratio of these two moduli of elasticity ($E/E_O$) provides an indication of the hardness of the tumor relative to the surrounding tissue.

It is known that the Young's or shear elasticity modulus of a tumor varies significantly from the modulus of elasticity for surrounding tissue. For example, carcinoma may have an elasticity modulus of 10 times the elasticity modulus of normal tissue. However, in some cases, the elasticity modulus of tumors may not be substantially different from that of normal tissue making the tumors "nonpalpable". FIGS. 5 and 5A illustrate that the differential pressure profile ratio, namely ($\Delta P/P_0$), (a change in amplitude of the pressure sensed at an inclusion divided by the pressure in that region of normal tissue) in the region surrounding the tumor is quite sensitive to changes in the elasticity modulus ratio ($E/E_O$).

In FIG. 5, a "block" of tissue 10 has a height H from a base to the contact point with the pressure sensors 15, and has a length L extending along the "X" direction (i.e., horizontal axis). A tumor 30 is positioned in the tissue 10, and is located a distance below the loading plate 12 equal to (h) and it has a diameter (d). Tumor 30 is located along the horizontal axis at a distance (a) from a left edge of the tissue 10.

FIG. 5A is a graph illustrating the differential pressure ratio ($\Delta P/P_0$) (values shown on the vertical axis), as a function of the distance along the X axis from the left edge of the tissue 10 to the right. The position of the tumor 30 at (a) is indicated by a vertical dotted line in FIG. 5A. Several plots of ($\Delta P/P_0$) as a function of (X/L) are shown, each corresponding to a given ratio of moduli of elasticity ($E/E_O$), which indicates the relative hardness between a tumor and normal tissue.

With the parameters having the values shown in FIG. 5A, the plots illustrate that a tumor/tissue combination having an elasticity moduli ratio ($E/E_O$) of only 1.5, i.e., the tumor having a modulus of elasticity of 1.5 times that of the surrounding tissue, a detectable change in the pressure signal of about 3% is observed for the region surrounding the tumor. This means that even tumors that are not much harder than surrounding tissue can be detected quite easily. It is known that a tumor in a breast, for example, can be detected by a palpation (which is the only technique available for evaluating elasticity), but palpation is reliable only when the tumor has progressed so its Young's modulus is more than five to ten times larger than that of surrounding tissue. The differential pressure signal ($\Delta P/P_0$) shows a more pronounced effect near the tumor when the elasticity moduli ratio ($E/E_O$) is 2 or 5 or more. However, in this case when the elasticity moduli ratio is greater than 7.5 (e.g., 10), there is not a substantial increase in the differential pressure profile above that shown for $E/E_O$=7.5.

When tumors or inclusions are softer than the surrounding tissue, e.g., the ratio ($E/E_O$) is 0.5, a substantial difference in the differential pressure profile ($\Delta P/P_0$) in the region of the tumor is readily observable. A more pronounced effect occurs when the ratio ($E/E_O$) is 0.25. Accordingly, by observing a relatively small change in the pressure profile (only 2-10%), one can detect tumors that have a relatively small change in the modulus of elasticity. This clinically significant data is obtained by using a pressure sensor array extending across the surface of the tissue and external to the tissue that measures a pressure profile response during compression of the tissue.

Figure 6:
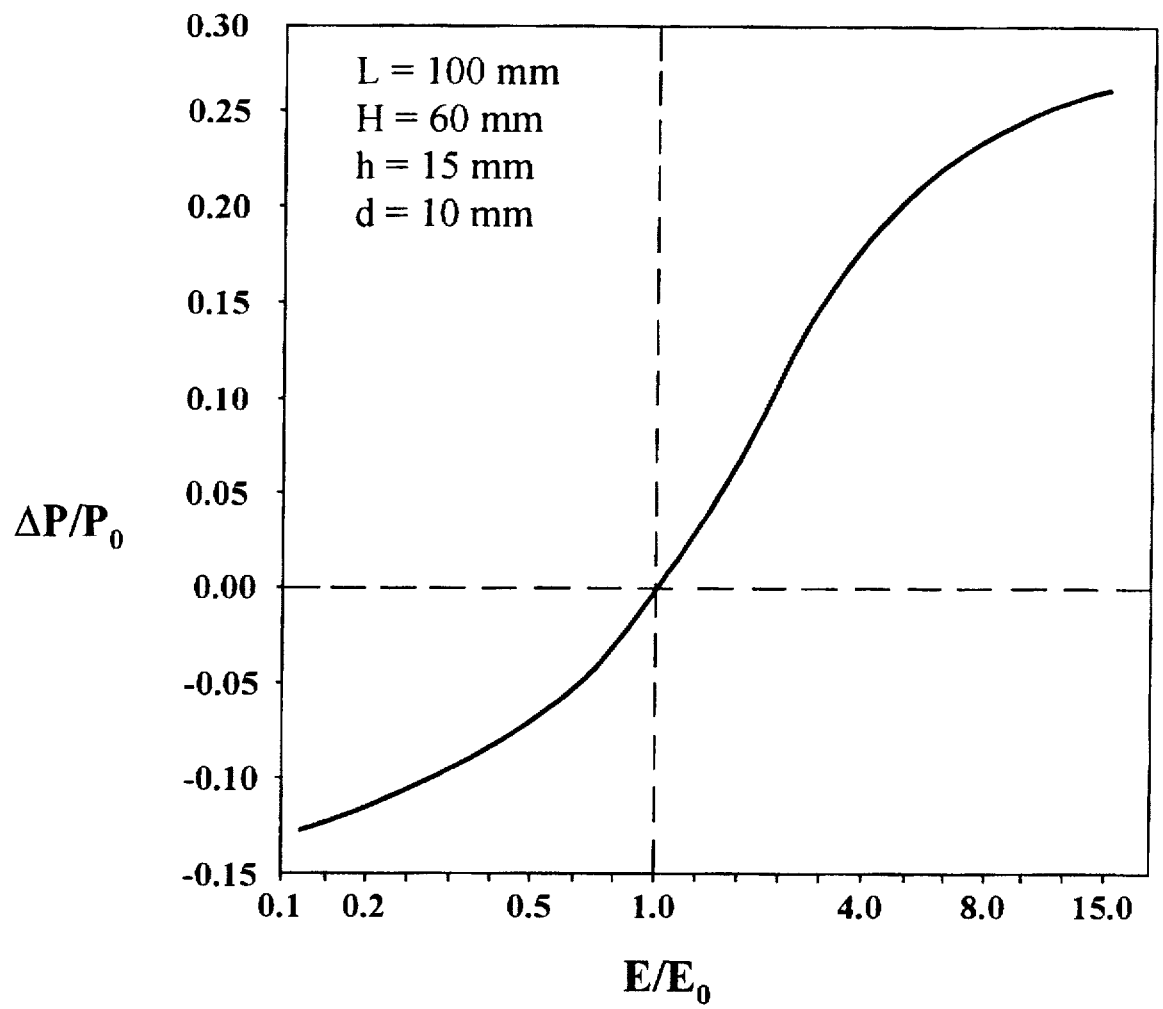
FIG. 6 a graphical representation of the calculated relationship between differential pressure ratio and moduli of elasticity ratios for a loading structure shown in FIG. 5.

FIG. 6 illustrates the changes in pressure sensed as a function of the change in the elasticity modulus ratio ($E/E_O$).

Similar to the illustration in FIGS. 5 and 5A, FIG. 6 shows that easily achievable resolution of a few percent in the pressure profile ratio ($\Delta P/P_0$) can enable one to detect inclusions differing from the surrounding tissue in hardness to an extent which does not permit palpatory detection. The graph is based on a tissue block 10 having the parameters such as indicated on FIG. 6. The values on the horizontal axis ($E/E_O$) are provided on a logarithmic basis to facilitate comparison purposes.

Figure 7:
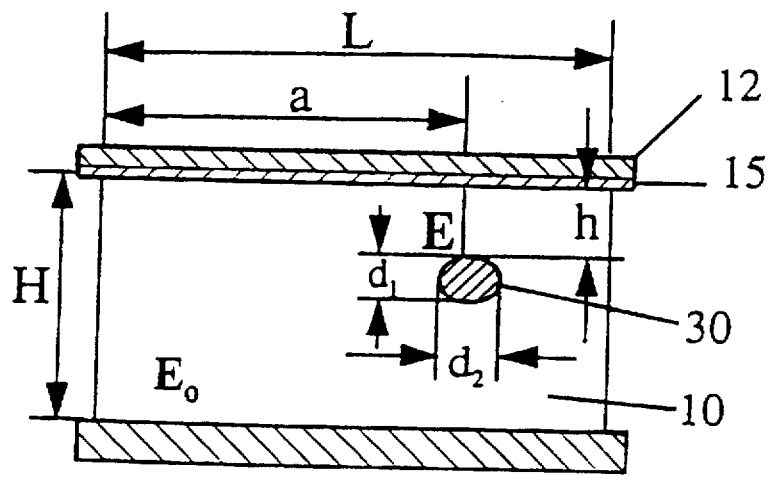
FIG. 7 is a schematic representation similar to that shown in FIG. 5 with certain loading parameters illustrated.
Figure 7A:
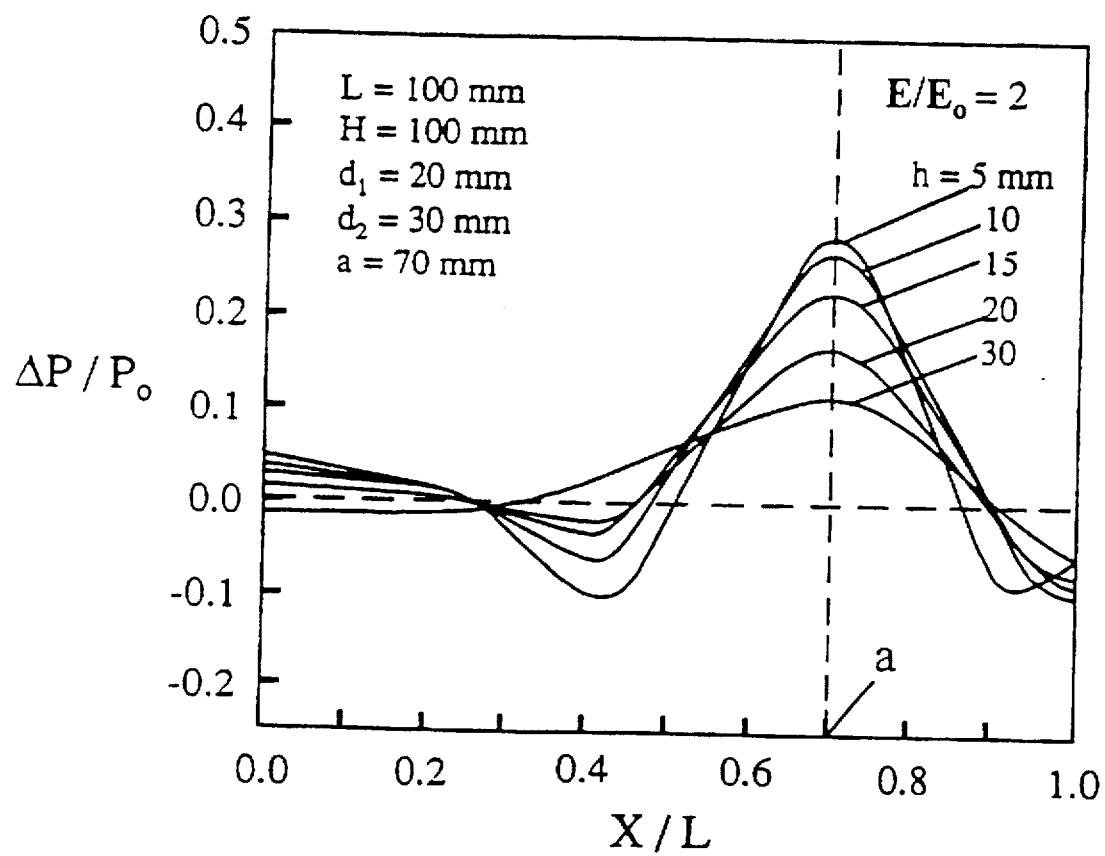
FIG. 7A is a graphical representation of the calculated differential pressure ratio across the surface at differing depths of a tumor in tissue shown at FIG. 7.

FIGS. 7 and 7A illustrate that the capability to detect a tumor within a block of tissue depends on the distance of the tumor from the tissue surface (skin) and pressure sensors. As seen in FIG. 7, the block of tissue 10 has a tumor 30' located therein and, in this instance, the vertical height of the tumor is represented as $d_1$ and the lateral width of tumor is represented as $d_2$. The parameter (a) represents the tumor's distance from its position from the left side of the tissue block. A set of values for the dimensions shown in FIG. 7 are listed in FIG. 7A. FIG. 7A shows the calculated plot of the pressure profile ratio ($\Delta P/P_0$) (the change in pressure of tumor tissue relative to normal tissue divided by the pressure sensed with no tumor) as a function of (X/L) along the X axis. This graph illustrates that a substantial change in the pressure profile ratio ($\Delta P/P_0$) of about 0.3 is observed when the tumor is a small distance (h=5 or 10 mm) from the tissue surface and that a smaller change in pressure profile ratio occurs when the tumor is far from the surface (e.g., h=30 mm). However, even when the tumor is deep (h=30 mm), the pressure profile ratio change is still readily discernible (with ($\Delta P/P_0$ about 0.1 which is quite measurable) to indicate a tissue abnormality at about X/L=0.70. The ratio of ($E/E_O$) is taken to be equal to 2.

Figure 8:
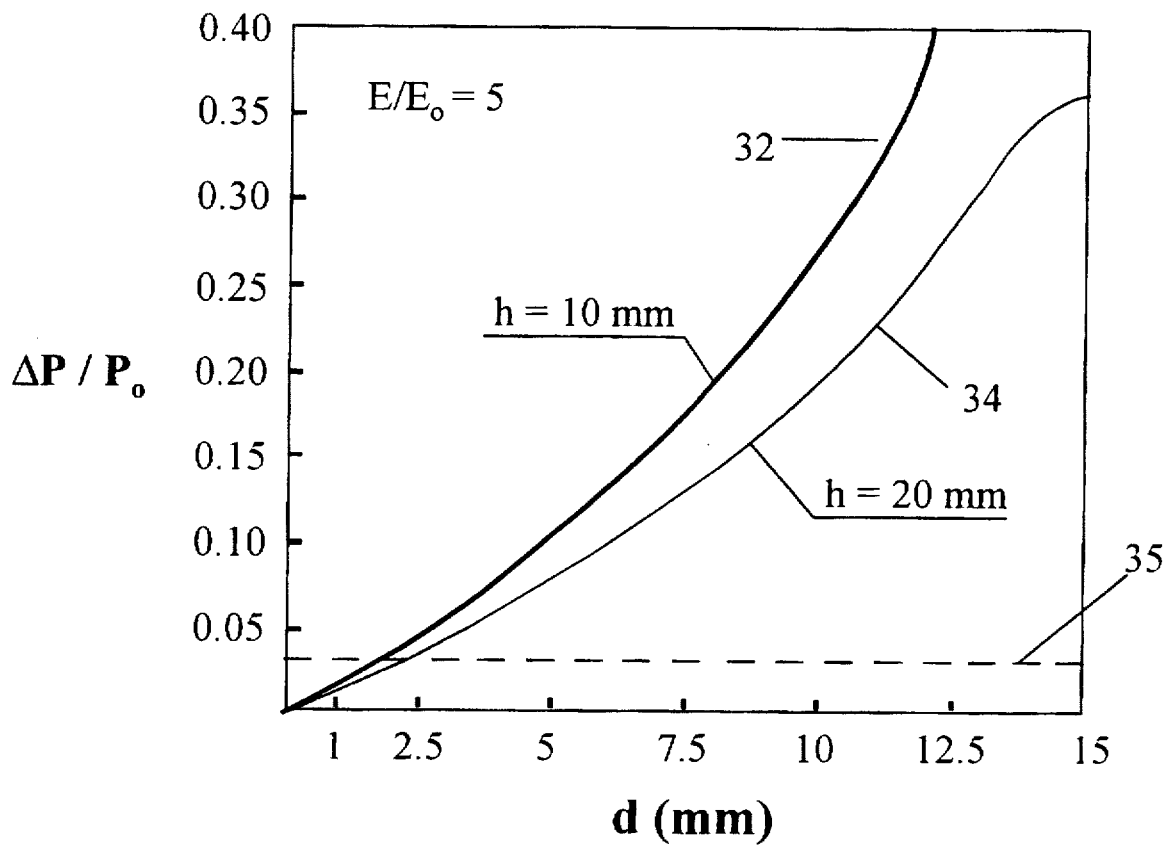
FIG. 8 graphical representation of calculated differential pressure ratio relative to the diameter of a tumor being sensed at differing depth of the tumor as shown in FIG. 5.

FIG. 8 illustrates the effect on the ability to ascertain a change in pressure with the sensors 15 as a function of the change in the diameter d of the tumor 30. As seen in FIG. 8, the elasticity moduli ratio ($E/E_O$) is equal to five, and the graph shows a plot of ($\Delta P/P_0$) versus d for a tumor with h=10 mm (indicated by line 32) and a tumor with h=20 mm (indicated by line 34). The pressure ratio ($\Delta P/P_0$) at the point of surface above the tumor, is indicated along the vertical axis, while the diameter of the tumor d is indicated along the horizontal axis.

The reference line indicated as 35 is more or less the base line for sensitivity of the ratio ($\Delta P/P_0$) measurement that can be easily obtained with existing pressure sensors. An accuracy of about three percent for pressure sensors is quite achievable, and the base line 35 represents a change of about three percent, which will give a clear indication of the presence of a tumor in normal tissue having a diameter (d) in the range of one to two millimeters. FIG. 8 indicates that, the larger the tumor, the greater is the change in the pressure ratio.

Figure 9:
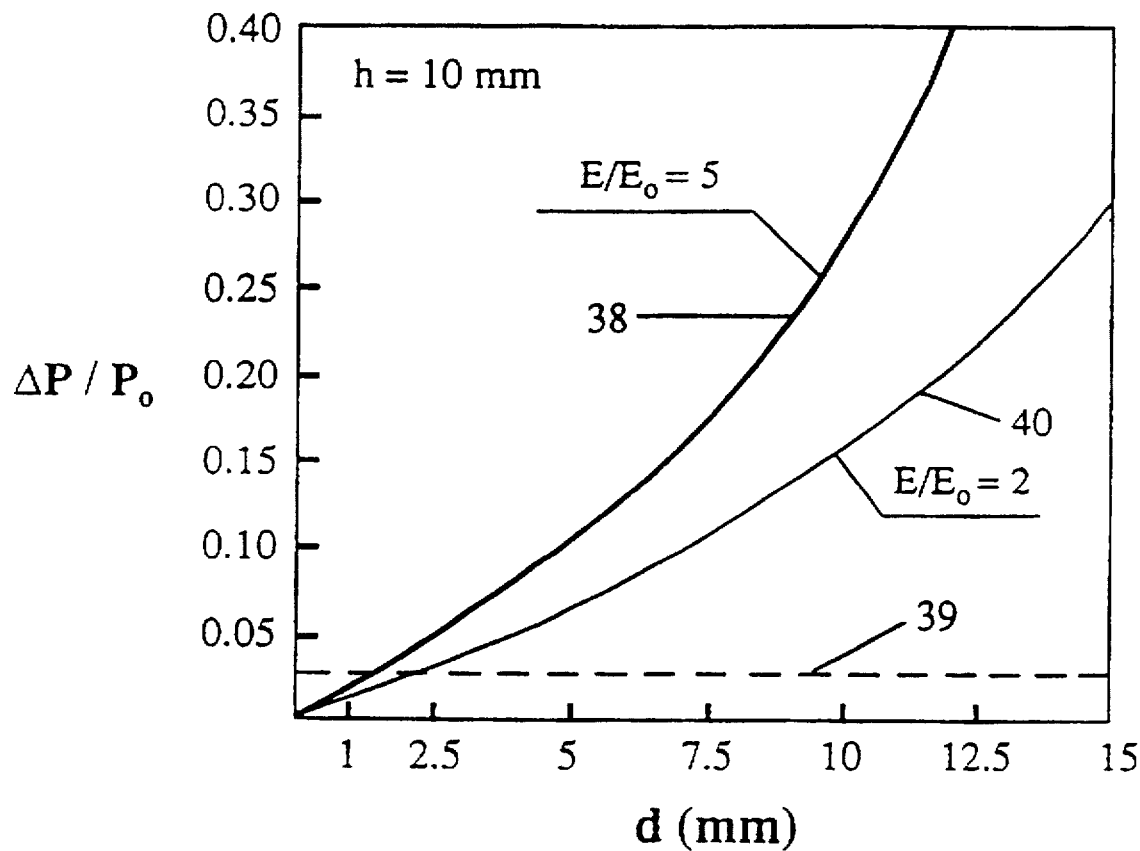
FIG. 9 is a graphical representation of the calculated differential pressure ratio relative to the diameter of a tumor, at differing ratios of moduli of elasticity between the surrounding tissue and the tumor.

FIG. 9 again illustrates the change in the pressure profile ratio ($\Delta P/P_0$) at the point of surface above the tumor as a function of the diameter (d) of the tumor. However, this time, the depth (h) of the tumor below the sensors 15 is set at 10 mm and a plot is provided for the case when the elasticity moduli ratio ($E/E_O$) equals 5 (indicated by upper curve 38) and when ($E/E_O$) equals 2 (indicated by lower curve 40). As expected, the greater the difference in the elasticity modulus between the tumor and surrounding tissue, (a larger ratio ($E/E_O$)), the more substantial change in the pressure profile ratio ($\Delta P/P_0$) for a given diameter tumor and the more easily the tumor will be detected. Taking the ratio ($\Delta P/P_0$) as an indication of sensitivity, one can observe line ($E/E_O=5$) crossing a threshold level of sensitivity (indicated by the dashed line at 39) indicating that detection of a tumor in the range of 1 mm can be made. When an elasticity modulus ratio is 2 (curve 40), one can observe that a tumor of 2.5 mm in diameter (d) could be detected. It is well known that palpation permits detection of tumors only if their diameter is over 8–10 mm, but not smaller. The graph in FIG. 9 shows quantitatively how the detection device (pressure sensors) becomes substantially more sensitive (on a relative basis, i.e., a larger change in the pressure profile ratio ($\Delta P/P_0$) is observed) as the elasticity moduli ratio ($E/E_O$) of the tumor tissue relative to the normal tissue increases.

FIGS. 10A–C, 11A–C, and 12A–C show sectional views and main elements of an embodiment of the transrectal Mechanical Imaging probe according to the present invention. Referring to the longitudinal view of the probe 100 shown in FIG. 10A, the probe 100 comprises a moveable tip 102 which contains an array of pressure sensors 101 and a position/orientation sensor 103 (sensing element of the 3SPACE® INSIDETRAK™ position/orientation tracking device made by Polhemus Inc., Colchester, Vt.). The resolution of the 3D position measurements achievable with this particular system is 0.2 mm, assuming that the maximum distance between the main electronic unit (fixed outside the probe) and the sensing element 103 (mounted inside of the tip 102 of the probe 100) is no more than 50 cm. The tip 102 of the probe 100 can be made significantly thinner than a finger of a physician. The tip 102 is mated to a rigid tube 111, which in turn is attached to a pistol grip handle 114. A disposable rubber sheath 113 covers the entire tip 102 as well as the tube 111. The electrical connections for the pressure sensor array as well as the position sensor are carried via a cable 112 (partly shown). A flexible joint between the tip 102 and the tube 111 shown in detail in FIG. 12 is provided to allow the tip to be articulated over angles ranging from 0° to ±45° vertically, and ±90° horizontally. The joint consists of disks 105 and 107 which allow vertical motion, and disks 108 and 110 which allow horizontal motion. Two stepper motors 121 and 122 within the handle drive control cables 106 and 109, thereby permitting positioning of the probe tip 102, based on operator commands. The probe 102 tip position is controlled by pressing the various buttons on the handle 114, a two-position switch for up/down 123, 124, and another two-position switch for left/right operation 125, 126. In addition to the stepper motors, the handle also contains a printed circuit board (PCB) with all electronics necessary for operating the motors, as well as a first stage of the data acquisition circuit. The control cables 106 and 109 are tensioned by two rollers 115 connected to tensioning springs 116. The springs 116 are mounted on a safety switch 117 which is connected to the handle via a safety spring 118. The resistance of the spring 118 is calibrated so that the forces experienced by the patient can never exceed certain safe limits. The operator can manually release the tension of the cables 106 and 109 by pulling on the safety switch 117 if there is any indication that the patient is experiencing discomfort or pain. In addition to this mechanical safety mechanism, it also is possible to use a sensor which will monitor the tension of the springs 116 and which will stop the motion of the stepper motors 121 and 122 if a preselected level of tension is reached.

Alternatively, a biopsy needle (not shown) can be provided on the probe 100 for taking a tissue sample.

FIGS. 11A–C and 12A–C are detail views of the probe tip and the joint which permits articulation of the probe tip. The pressure sensor 101 for transrectal probe for use in the prostate transrectal probe 100 employs a polyvinylidene fluoride (PVDF) piezoelectric film (such as manufactured by AMP Inc., Valley Forge, Pa.). Other pressure sensors may be used. However, the PVDF film pressure sensors are highly sensitive, easy to work with, provide excellent matching with soft biological tissue and are readily available. There are several ways in which the PVDF film can be mounted on the tip 102 of the transrectal probe 100 to serve as a pressure sensor. In one of the possible patterns of the sensor arrangement (FIG. 11C), there are two long 1×12 mm sensors on each side of the array. These are used to provide information on how evenly the pressure is applied over the array. This information is displayed to the operator so that he or she can adjust the position of the sensor during examination to provide a more even pressure distribution. It can also be used to filter out those points of the collected data which were obtained with the array tilted relatively to the surface of the prostate.

Figure 13:
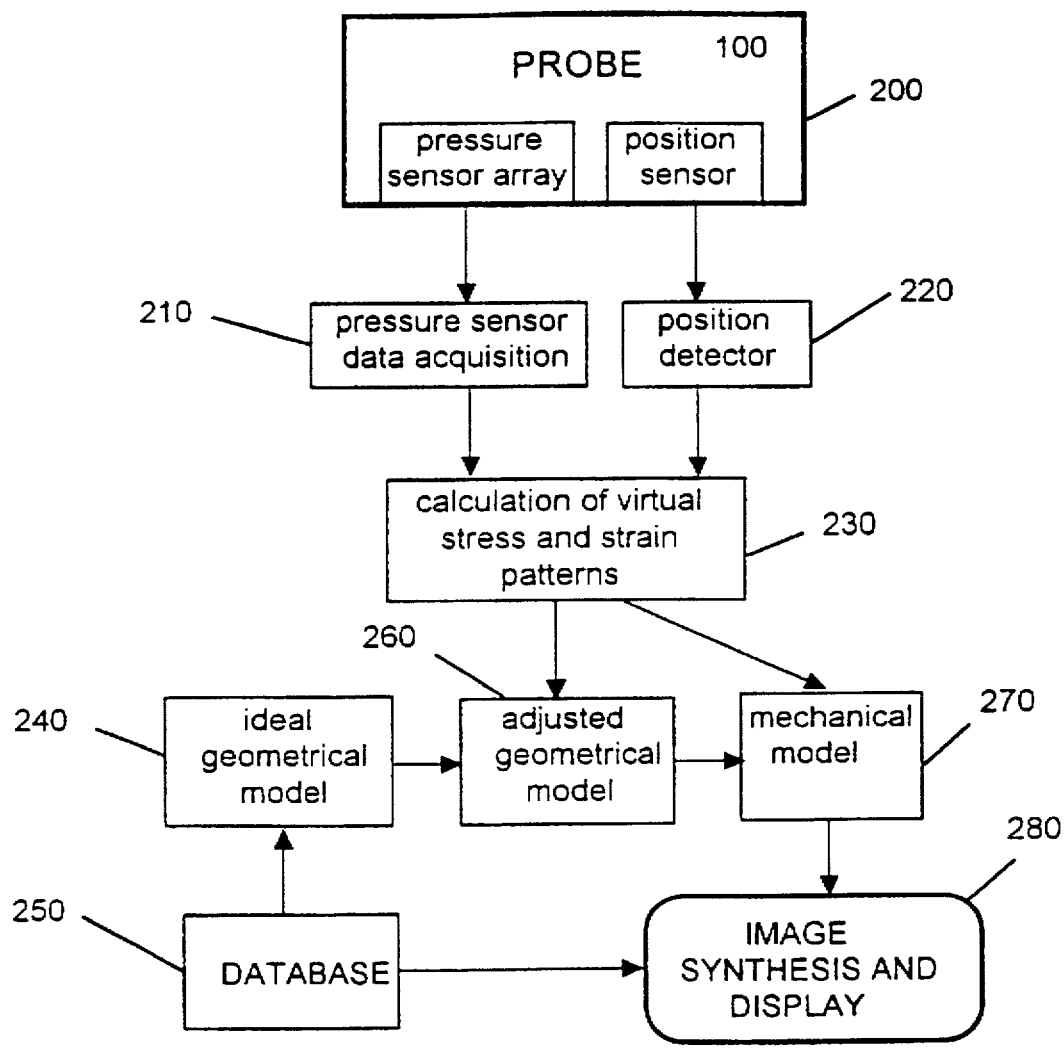
FIG. 13 is a schematic diagram of the method and apparatus in accordance with the present invention.

FIG. 13 is a schematic diagram showing the processing of signals 200 from the probe 100. Pressure sensor data 210 and position/orientation sensor data 220 are combined for calculating the virtual patterns of stress and strain 230. An ideal geometrical model 240 of the prostate is generated from a database 250 and is further adjusted to match the estimated dimensional parameters of the examined prostate. Using this adjusted geometrical model 260 theoretical patterns of stress and strain are evaluated and compared with the respective virtual stress and strain patterns, with the differences being used to create a mechanical model 270 of the prostate. This mechanical model with addition of relevant data from the database is used to create and display an image 280.

The geometric model of the tissue can be adjusted by varying a spatial distribution of elasticity in the geometric model to minimize the differences between the virtual pattern of at least one property taken from the group of properties of stress and strain and the respective theoretical pattern from the adjusted geometric model, thereby obtaining a spatial distribution of elasticity modulus in the tissue portion.

Figure 14A:
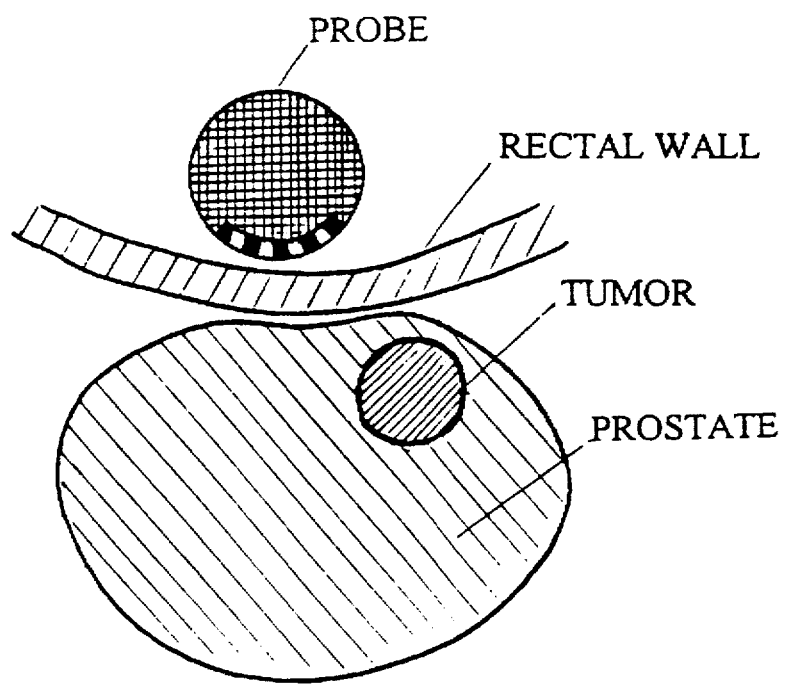
FIG. 14A is a sectional view showing the relationship of the probe, rectal wall, and prostate with internal nodule.
Figure 14B:
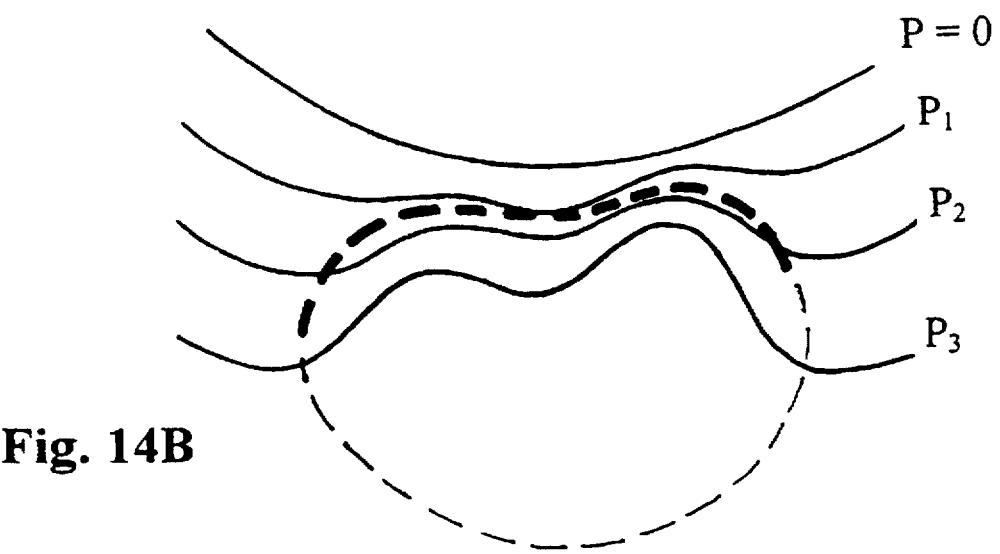
FIG. 14B a schematic diagram showing virtual lines of equal pressure calculated from the data obtained using the position sensor and pressure sensor array of the present invention.

FIG. 14A shows the relationship of the probe, rectal wall, and a prostate with a nodule in cross section. FIG. 14B illustrates the virtual lines of equal pressure calculated from the data obtained by the position sensor and pressure sensor array. Equal pressure lines denoted in FIG. 14B as P=0, $P_1$, $P_2$, and $P_3$ which correspond to different levels of pressure, are related to the virtual strain profile. A fraction of the prostate contour shown in FIG. 14B by the bold dotted line is reconstructed using the equal pressure profile data and the nonlinearity of the strain/stress relationship. At low level of pressures when the compression is related mainly to the motion of the rectal wall tissue the system behaves linearly. At a certain level of compression the slope of the strain/stress curve exhibits sharp increase reflecting the resistance of the prostate tissue. In each region over the prostate there is a point in the space where the strain/stress relationship starts to change sharply its slope. The surface formed by these points corresponding to a certain level of nonlinearity of the strain/stress relationship is determined by the geometrical parameters of the examined prostate and can be used for estimating the contour of the prostate shown in FIG. 14B by dotted line. The data shown schematically in the FIG. 14B can also be used to evaluate the virtual stress pattern. The virtual stress pattern is obtained by calculating the values of pressure that correspond to the points on the surface shown by dotted line. Both virtual strain and virtual stress profiles are further used to form a mechanical model of the examined prostate using additionally relevant information from a general database, as shown in FIG. 13.

In traditional medical imaging, the device usually displays the structure of an object in terms of some measured physical property. The image obtained this way is often very far from what the actual examined region of body or an organ would look like if exposed to direct sunlight, or drawn by an artist. Therefore, an expert in a particular type of image analysis is required to tell the physician what information from the image is relevant to the diagnosis. Currently, as a result of a wider use of powerful computer means and databases, an alternative approach to imaging, so called Knowledge-Based Imaging (Sarvazyan et al., *A new philosophy of medical imaging*, Medical Hypotheses 36, 327-335, 1991, incorporated herein by reference) has started to emerge. The method of the present invention includes the use of the knowledge-based approach briefly described below. Using knowledge-based imaging, a computer can store in memory a 3D picture of a "normal" prostate which is being examined, and adjust (transform) this image according to the measured data, to produce an image that represents the actual examined gland. Such a pictorial 3D image or its cross sections will additionally include data on the mechanical properties of the prostate. It will be significantly easier for a physician to recognize abnormalities of the examined organ, represented on such an image. Further, the expert system will use the knowledge about characteristics of different types and stages of prostate cancer to point out any poorly defined and suspicious regions in the model, or just show any abnormalities or deviations from what the "normal" prostate should look like. At this point, the physician can also enter into the computer new information based on other tests or exams performed on the same prostate, and the knowledge base will "learn" and "expand."

Once a 3D model of the actual examined prostate is stored in the computer, it must be presented by the user in a way that would allow both external and internal features to be seen on one picture. This means that the 3D image on the screen should contain information about geometrical features of the prostate as well as spatial distribution of elasticity and surface texture information. Additionally, the image should indicate to the user which areas of the examined prostate are poorly defined and need to be examined further in order to produce a complete diagnosis. There are several potential 3D visualization methods that can be suitable for this task, such as polygon based surface methods, ray cast volume rendering and cross section slicing.

Although certain presently preferred embodiments of the present invention have been specifically described herein, it will be apparent to those skilled in the art to which the invention pertains that variations and modifications of the various embodiments shown and described herein may be made without departing from the spirit and scope of the invention. Accordingly, it is intended that the invention be limited only to the extent required by the appended claims and the applicable rules of law.

What is claimed is:

1. A method of identifying a region within a tissue portion accessible from a tubular body conduit having a different elasticity than the surrounding tissue, said method comprising the steps of:

causing a deformation of the tissue portion for causing stress and strain in the tissue portion, said deformation caused by applying pressure with a pressure applying means over a plurality of locations over the examined tissue portion in a manner similar to the pressure applied by a human finger; measuring a localized pressure distribution in a plurality of regions of tissue;

determining positions of said pressure applying means corresponding to each said measured localized pressure distribution;

calculating a virtual pattern of at least one property taken from the group of properties consisting of stress and strain using said localized pressure distributions and said corresponding positions;

defining a geometrical model of the tissue portion having homogeneous tissue and given boundary conditions for the tissue portion;

evaluating a theoretical pattern of said at least one property of stress and strain for said geometrical model;

comparing said theoretical pattern and said virtual pattern to obtain the difference between said patterns, this difference indicating the presence and location of a differing elasticity region of the tissue within the tissue portion; and adjusting said geometrical model by varying a spatial distribution of elasticity in said geometrical model to minimize differences between the virtual pattern of at least one property taken from the group of properties consisting of stress and strain and the respective theoretical pattern for said adjusted geometrical model, thereby obtaining a spatial distribution of elasticity modulus in the tissue portion.

2. The method of claim 1, wherein the deformation is caused by movement of the pressure applying means in a plurality of degrees of freedom within the tubular body conduit.

3. The method of claim 1, wherein the tubular body conduit is of size to receive an articulated probe having a pressure sensing array oriented on said probe so as to sense pressure at a plurality of locations on an interior surface of the tubular conduit and a position sensor to determine said locations.

4. The method of claim 1, wherein the tubular body conduit is the human rectum and the tissue portion is the human prostate gland.

5. A device for identifying a region within a tissue portion accessible from a tubular body conduit having a different elasticity than the surrounding tissue, said device comprising:

means for causing a deformation of the tissue portion, thereby causing stress and strain in the tissue portion, said deformation caused by a pressure applying means for applying pressure in a manner similar to the pressure applied by a human finger;

means for measuring a localized pressure in a plurality of regions of tissue;

means for determining positions of said pressure applying means corresponding to each said measured localized pressure;

means for calculating a virtual pattern of at least one property taken from the group of properties consisting of stress and strain using localized pressure and said corresponding positions;

means for defining a geometrical model of the tissue portion having a homogeneous tissue and given boundary conditions for the tissue portion;

means for evaluating a theoretical pattern of said at least one property of stress and strain for said geometrical model;

means for comparing said theoretical pattern and said virtual pattern to obtain the difference between said patterns, this difference indicating the presence and location of a differing elasticity region of the tissue within the tissue portion; and means for adjusting said geometrical model by varying a spatial distribution of elasticity in said adjusted geometrical model to minimize differences between the virtual pattern of stress and strain and the adjusted geometrical model, thereby obtaining a spatial distribution of elasticity modulus in the tissue portion.

6. The device of claim 5, wherein the pressure applying means is articulated so as to be movable in a plurality of degrees of freedom within the tubular body conduit.

7. The device of claim 5, wherein the pressure applying means is an articulated probe having a pressure sensing array oriented on said probe so as to sense pressure pattern at a plurality of locations on an interior surface of the tubular body conduit.

8. A device for mechanical imaging the human prostate gland comprising:

an articulated tip having a plurality of degrees of freedom;

said articulated tip configured so as to be insertable within the human rectum so as to be proximate to the human prostate gland, said articulated tip being movable within the rectum so as to press against regions of the prostate gland and to deform the tissue in the region of the prostate gland;

a position sensor mounted in the articulated tip for determining positions of said articulated tip;

a pressure sensing array comprising a plurality of pressure sensors mounted on the articulated tip and oriented so as to detect a local pressure pattern over the tissue being deformed by the articulated tip; and means for processing signals detected by said pressure sensing array and said position sensor, so as to obtain a spatial distribution of geometrical and mechanical properties of the prostate.

9. A device as in claim 8, wherein said geometrical and mechanical properties of the prostate are selected from the group of properties consisting of size, shape, contour, asymmetry, global hardness, nodularity, consistency and spatial distribution of the elasticity modulus.

10. A device as in claim 8, wherein the pressure sensing array is comprised of a plurality of individual sensors each made of a piezoelectric polymer film.

11. A device as in claim 8, wherein said position sensor wireless position sensor.

* * * * *